United States Patent [19]
Fleck et al.

[11] 3,956,280
[45] May 11, 1976

[54] PYRAZOLINE COMPOUNDS

[75] Inventors: Fritz Fleck, Bottmingen, Basel-Land, Switzerland; Peter Stuart Littlewood, Ilkley; Alec Victor Mercer, Leeds, both of England

[73] Assignee: Sandoz Ltd., Basel, Switzerland

[22] Filed: Oct. 20, 1974

[21] Appl. No.: 534,799

Related U.S. Application Data

[63] Continuation of Ser. No. 272,422, July 17, 1972, abandoned.

[30] Foreign Application Priority Data

| July 19, 1971 | Switzerland | 10577/71 |
| Oct. 13, 1971 | Switzerland | 14977/71 |
| Oct. 25, 1971 | Switzerland | 15546/71 |

[52] U.S. Cl. ............... 260/239.65; 260/239.9; 260/243 B; 260/310 D; 260/311; 252/301.27; 8/1 W; 8/54.2; 8/177 R; 8/178 R
[51] Int. Cl.² .............................. C07D 231/06
[58] Field of Search ........... 260/243 B, 310 D, 311, 260/239, 65, 239.9; 252/301.2 W, 301.3 W

[56] References Cited
UNITED STATES PATENTS

| 189,772 | 1/1975 | Boehuke et al. | 260/310 D |
| 3,131,079 | 4/1964 | Wagner et al. | 260/310 D |
| 3,141,879 | 7/1964 | Housermann et al. | 260/310 D |
| 3,629,241 | 12/1971 | Krause et al. | 260/259.9 |
| 3,849,406 | 11/1974 | Aebli et al. | 260/239.65 |
| 3,852,275 | 12/1974 | Domergue et al. | 260/239.9 |

FOREIGN PATENTS OR APPLICATIONS

| 1,111,986 | 5/1968 | United Kingdom | 260/239.9 |
| 1,461,687 | 11/1966 | France | 260/556 B |

OTHER PUBLICATIONS
Chemical Abstracts, 65:5572 (2) 1966, Hoechst.

*Primary Examiner*—Sherman D. Winters
*Attorney, Agent, or Firm*—Gerald D. Sharkin; Richard E. Villa; Thomas C. Doyle

[57] ABSTRACT
The invention provides novel pyrazoline derivatives which are useful as optical brighteners.

17 Claims, No Drawings

PYRAZOLINE COMPOUNDS

This is a continuation of application Ser. No. 272,422 filed July 17, 1972, now abandoned.

PYRAZOLINE COMPOUNDS

This invention relates to pyrazoline compounds of formula

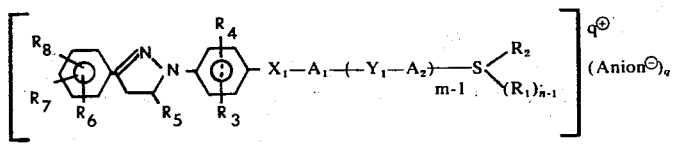

(I).

where $X_1$ signifies $-SO_2-$, $-CO-O-$ or $-SO_2-NH-$, $Y_1$ signifies

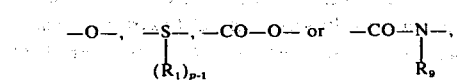

$A_1$ and $A_2$ each signifies alkylene with 1 to 3 carbon atoms, $R_1$ signifies a lower, optionally substituted alkyl radical, $R_2$ signifies a lower, optionally substituted alkyl radical or an optionally substituted cycloalkyl or aryl radical, $R_3$ and $R_4$, independently of each other, each signifies a hydrogen or halogen atom or a lower alkyl or alkoxy radical, $R_5$ signifies a hydrogen atom, an optionally substituted lower alkyl radical or an optionally substituted phenyl radical, $R_6$, $R_7$ and $R_8$ each signifies, independently of the others, a hydrogen or halogen atom or a lower alkyl or alkoxy radical, or optionally substituted aryl radical, a cyano or carboxylic acid group, an optionally substituted carboxylic acid amide, carboxylic acid ester, sulphonic acid amide or sulphonic acid ester group or an acylamino group, $R_9$ signifies hydrogen or a lower, optionally substituted alkyl radical, $m$, $n$, and $p$ each signifies the integer 1 or 2, $q$ signifies the number of radicals $R_1$ present, and anion$^\ominus$ signifies an equivalent of a colourless anion, with the provision that if $m$ has the value 2 and $Y_1$ represents

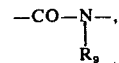

$R_2$ and $R_9$ may jointly form an alkylene bridge member containing 1 to 3 carbon atoms, and also provided that when $X_1$ is $SO_2-$, $A_1$ is $-CH_2CH_2-$ and $m$ is 1, than $n$ is 2.

Compounds of formula (I) in which $m$ is 2 and $Y_1$ represents $-COO-$ or

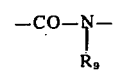

can be produced by acylation of a compound of formula

where $Y_2$ represents $-O-$ or

with a carboxylic acid of formula

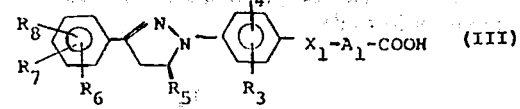

or with a halide, anhydride or ester of this acid, if necessary with treatment of the acylation product with an alkylating agent of formula $$R_1-R_{10} \qquad (IV),$$

where $R_{10}$ represents a radical convertible into an anion.

Compounds of formula (I) in which $m$ is 2 and $Y_1$ represents $-CO-O-$ can be produced by reaction of a compound of formula

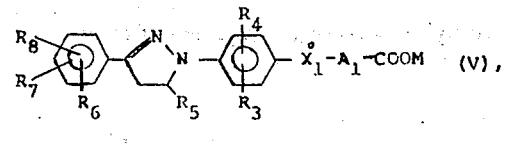

where M represents a metal equivalent, with a compound of formula

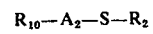

if necessary with treatment of the reaction product with an alkylating agent of formula (IV).

Compounds of formula (I) in which $X_1$ represents $-SO_2-$ and $Y_1$ $-O-$ or

can be produced by reaction of a compound of formula

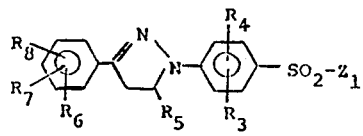 (VII), where $Z_1$ represents $-CH=CH_2$ or $-A_1-R_{10}$, with a compound of formula

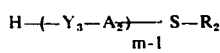 (VIII), where $Y_3$ represents $-O-$ or $-S-$, if necessary with treatment of the reaction product with an alkylating agent of formula (IV).

Compounds of formula (I) in which $X_1$ represents $-CO-O-$ can be produced by reaction of a compound of formula

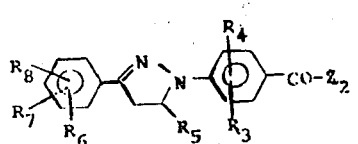 (IX), where $Z_2$ represents $-OH$, $-F$, $-Cl$ or $-Br$, with an alcohol of formula

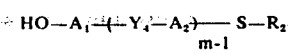 (X), where $Y_4$ represents $-O-$, $-S-$, $-CO-O-$ or

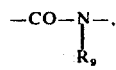

or by reaction of a compound of formula

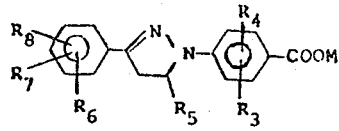 (XI)

with a compound of formula

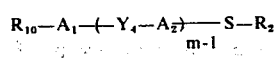 (XII), if necessary with treatment with an alkylating agent of formula (IV).

Compounds of formula (I) in which $X_1$ in which $X_1$ represents $-SO_2-NH-$ can be produced by reaction of a sulphonic acid halide of formula

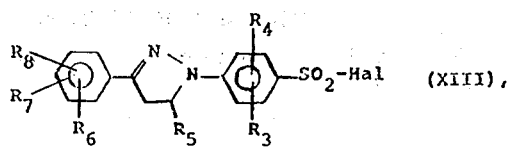 (XIII), where Hal represents $-F-$, $-Cl$ or represents formula $H_2N-A_1-(-Y_4-A_2)_{m-1}-S-R_2$ (XIV), if necessary with treatment with an alkylating agent of formula (IV).

Compounds of formula (I) in which $R_5$ represents hydrogen or an optionally substituted, lower alkyl radical can be produced by reaction of a compound of formula

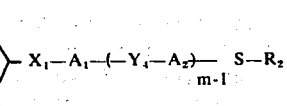 (XV), where $R_{11}$ represents hydrogen or an optionally substituted, lower alkyl radical and Q represents halogen or the N-bound radical of an amine suitable for the formation of a Mannich base or $-NH_2$, with a compound of formula $H_2N-NH-$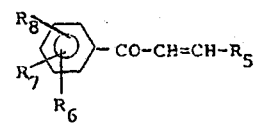

$H_2N-NH$-(ring with $R_4$, $R_3$)$-X_1-A_1-(-Y_4-A_2)_{m-1}-S-R_2$ (XVI), or its acid adduct, if necessary with treatment of the reaction product with an alkylating agent of formula (IV).

Finally, compounds of formula (I) can be produced by reaction of a compound of formula

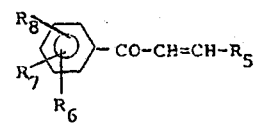 (XVII), with a compound of formula (XVI) or its acid adduct, if necessary with treatment with an alkylating agent of formula (IV).

The process of production for compounds of formula (I) is characterized by the above reactions and comprises conversion of the substituents into other substituents coming within the given definitions, in particular the conversion of nitrile groups into carboxylic acid amide groups and the hydrolysis of carboxylic acid amide or ester groups to free carboxylic acid groups and the replacement of an anion⁻ by another anion⁻.

As examples of bridge members $A_1$ and $A_2$, which are independent of each other in significance, the following may be named: —CH₂—, —CH₂—CH₂—, —CH₂CH₂—CH₂—,

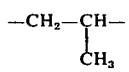

and

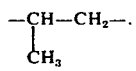

Suitable halogen atoms (substituents $R_3$, $R_4$, $R_6$, $R_7$ and $R_8$) are, for example, fluorine and preferably chlorine atoms.

Especially suitable lower, unsubstituted alkyl radicals (substituents $R_1$ to $R_9$ and $R_{11}$) are straight-chain or branched radicals containing 1 to 8 carbon atoms, e.g. methyl, ethyl, iso-propyl, n-propyl, n-butyl, sec. butyl, tert. butyl, iso-butyl, n-amyl, iso-amyl, sec. amyl, tert. amyl, n-hexyl, n-octyl, iso-octyl and 2-ethylhexyl; the alkyl radicals contain preferably 1 to 5 carbon atoms and are not branched; methyl and ethyl are especially preferred.

Especially suitable substituted alkyl radicals (substituents $R_1$, $R_2$, $R_5$, $R_9$ and $R_{11}$) are alkyl radicals containing 1 to 8 carbon atoms as described above, which bear as substituents halogen atoms, phenyl radicals, alkoxyalkoxy groups or preferably lower alkoxy groups with 1 to 4 carbon atoms, hydroxyl, cyano, alkenyl, carboxyl, aminocarbonyl or epoxy groups. The following radicals may be named as examples: 2-chloroethyl, 2,2-difluoroethyl, trifluoromethyl, cyanomethyl, 2-cyanethyl, 2-hydroxyethyl, 2- and 3-hydroxypropyl, 2-methoxy, 2-ethoxy- and 2-n-butoxyethyl, 3-methoxypropyl, 4-methoxybutyl, 2-(2'-methoxyethoxyl)-ethyl, benzyl, 2-phenylethyl, carboxymethyl, epoxymethyl and 2,3-propenyl-1. But the alkyl radicals are preferably unsubstituted.

Especially suitable lower alkoxy radicals (substituents $R_3$, $R_4$, $R_6$, $R_7$ and $R_8$) are optionally branched alkoxy radicals containing 1 to 8 carbon atoms, e.g. methoxy, ethoxy, n-propoxy, iso-propoxy, n-butoxy, n-amyloxy and n-octyloxy; the alkoxy radicals contain preferably 1 to 5 carbon atoms and are not branched; methoxy is especially preferred.

Suitable cycloalkyl radicals (substituent $R_2$) are cyclohexyl and methylcyclohexyl.

The aryl radicals (substituents $R_2$, $R_6$, $R_7$ and $R_8$) may be, for example, dinuclear radicals such as naphthyl-1, naphthyl-2 and diphenyl-4 or in particular mononuclear, optionally substituted aryl radicals such as phenyl, 2-, 3- or 4-methylphenyl, 2-, 3- or 4-chlorophenyl, 2- or 4-methoxyphenyl, 2- or 4-ethoxyphenyl, 4-fluorophenyl, 4-ethyl, 4-iso-propyl, 4-tert. butyl, 4-tert. amyl, 4-tert. octylphenyl, 2,4- or 2,5-dimethylphenyl, 2-, 3- or 4-carboxyphenyl, 2-, 3- or 4-cyanophenyl, 2-, 3- or 4-aminocarbonylphenyl, 2-, 3- or 4-methylaminocarbonylphenyl, 2-, 3- or 4-dimethylaminocarbonylphenyl, 2-, 3- or 4-methoxy, -ethoxy-, -n-butoxy-, -benzyloxy-, -cyclohexyloxy-, -phenoxy- or -cresoxy-carbonylphenyl, 3- or 4-sulphophenyl, 3- or 4-amino-, -methylamino- or dimethylamino-sulphonylphenyl, 3- or 4 -methoxy-, -ethoxy-, -n-butoxy-, -benzyloxy-, -cyclohexyloxy-, -phenoxy- or -cresoxy-sulphonylphenyl.

If $R_5$ is an optionally substituted phenyl radical it may have any of the relevant meanings given for $R_2$, $R_6$, $R_7$ and $R_8$.

The phenyl radicals preferably contain as substituents one or two chlorine atoms, one cyano group or one lower alkyl or alkoxy group, preferably methyl or methoxy.

If $R_2$ and $R_9$ jointly signify a lower alkylene bridge member, this contains preferably 1 to 3, in particular 2, carbon atoms, and the group

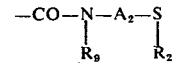

is then, e.g.

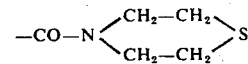

(carboxylic acid thiomorpholide).

Examples of suitable optionally substituted carboxylic acid ester groups (as substituents $R_6$, $R_7$ and $R_8$) are the carboxylic acid alkylester groups with 1 to 8 carbon atoms in the alkyl radical which may be substituted by alkoxy, phenyl or phenoxy radicals, the carboxylic acid cycloalkylester groups and the carboxylic acid arylester groups, preferably those of the naphthalene, diphenyl and in particular the benzene series. Examples of such carboxylic acid ester groups are methyl, ethyl, n-propyl-, iso-propyl, n-butyl-, iso-butyl, n-amyl-, iso-amyl-, n-hexyl-, n-octyl-, 2-ethylhexyl-, 2-methoxyethyl-, 2-ethoxyethyl-, 2-n-butoxyethyl-, 2-(2'-methoxyethoxy)-ethyl-, 2-(2'-ethoxyethoxy)-ethyl-, 2-(2'-n-butoxyethoxy)-ethyl-, benzyl-, 2-phenylethyl-, 2-phenoxyethyl-, cyclohexyl-, 4-methylcyclohexyl-, 4-diphenylyl-, naphthyl-1-, naphthyl-2-, phenyl-, 2-, 3- and 4-methylphenyl-, 2-, 3- and 4-chlorophenyl-, 2- and 4-methoxy- and -ethoxyphenyl-, 4-fluorophenyl-, 2,4- and 2,5-dimethylphenyl-, 4-n-butylphenyl-, 4-tert. butylphenyl-, 4-tert. amylphenyl- and 4-tert. octylphenylester groups.

The carboxylic acid ester groups are preferably lower, unsubstituted alkylester groups, in particular —COOCH₃ and —COOC₂H₅.

The sulphonic acid ester groups corresponding to the aforesaid carboxylic acid ester groups are suitable as optionally substituted sulphonic acid ester groups (as substituents $R_6$, $R_7$ and $R_8$).

Examples of suitable optionally substituted carboxylic acid amide or sulphonic acid amide groups (substituents $R_6$, $R_7$ and $R_8$) are amide, mono- and dialkylamide, mono- and di-(hydroxyalkyl)-amide, alkoxyalkylamide, alkoxyalkoxyalkylamide, aryl-, aralkyl-, aryloxyalkyl- and cycloalkylamide, N-alkyl- and N-hydroxylalkyl-N-phenylamide groups in which alkyl and hydroxyalkyl contain, for example, 1 to 8 or preferably 1 to 4 carbon atoms; alkoxyalkyl and alkoxyalkoxyalkyl contain preferably 3 to 6 or 5 to 8 carbon atoms, aryl and aryloxy may be dinuclear or preferably mononuclear. Specific examples are the carboxylic or sulphonic acid methyl-, ethyl-, n-propyl-, iso-propyl-, n-butyl-, sec. butyl-, iso-butyl-, n-amyl-, n-hexyl-, iso-amyl-, dimethyl-, diethyl-, di-n-butyl-, 2-hydroxyethyl-, 2- and 3-hydroxypropyl-, 4-hydroxybutyl-, di-(2-hydroxyethyl)-, di-(2-hydroxylpropyl)-, 2-methoxyethyl-, 2-ethoxyethyl-, 2-n-butoxyethyl-, 3-methoxypropyl-, 4-methoxybutyl-, 2-(2'-methoxyethoxy)-ethyl-, -2-(2'-ethoxyethoxy)-ethyl-, 2-(2'-n-butoxyethoxy)-ethyl-, phenyl-,-2-, -3- and -4-chlorophenyl-, 2- and 4-methoxyphenyl-, 2 - and 4-ethoxyphenyl-, 4-tert. butylphenyl-, 4-n-butylphenyl-, 2,4- and 2,5-dimethylphenyl-, 4-diphenylyl-, naphthyl-1-, naphthyl-2-, N-methyl-N-phenyl-, N-ethyl-N-phenyl-, N-2-hydroxyethyl-N-phenyl-, cyclohexyl-, 4-methylcyclohexyl-, benzyl-, phenylethyl- and phenoxyethyl-amide groups.

The carboxylic acid amide groups are preferably substituted by lower alkyl radicals (with 1 to 4 carbon atoms, preferably methyl), or are unsubstituted.

Examples of suitable acylamino groups (substituents $R_6$ to $R_8$) are optionally substituted, lower (containing 2 to 8 carbon atoms) alkanoylamino and alkoxycarbonylamino groups, optionally substituted benzoylamino, phenylsulphonylamino and alkylsulphonylamino groups (acetylamino, propionylamino, butyrylamino, methoxy- and ethoxy-carbonylamino, benzoylamino, 4-methyl- and 4-chloro-benzoylamino, phenylsulphonylamino, 4-methylphenylsulphonylamino, methyl- and ethyl-sulphonylamino). Acyl represents preferably a lower alkancyl radical with 2 to 5 carbon atoms.

The substituent $R_{10}$ is preferably a halogen atom (chlorine, bromine, iodine) or a sulphate, methylsulphate, ethylsulphate or sulphonate radical (methanesulphonate, ethanesulphonate, benzenesulphonate, 4-methylbenzenesulphonate). or an alkanoate radical (acetate, propionate) or a benzoate radical.

Organic and inorganic ions are suitable as colourless anions, for example the formate, acetate, chloracetate, propionate, oxalate, lactate, tartrate, benzoate, maleinate ions and the chloride, bromide, iodide, perchlorate, methylsulphate, ethylsulphate, methylsulphonate, sulphate, bisulphate, benzenesulphonate, 4-methylbenzenesulphonate, 4-chlorobenzenesulphonate ions. Also suitable are water-soluble double salt compounds with inorganic salts such as zinc chloride.

In the compounds of formula (I) in which n signifies 2 the anion formed in alkylation can be replaced by a different anion, for example by dissolving the compound in water or in an aqueous-organic medium and adding a silver salt (silver nitrate, acetate) if a halogen anion (Cl⁻, Br⁻, I⁻) is to be replaced by another anion, or by adding a barium salt if a different anion is to be introduced in place of a sulphate anion. This exchange can be effected with the aid of ion exchangers or in more than one stage, e.g. through the carbonate or hydroxide.

The preferred compounds of formula (I) are those which bear as substituents $R_3$ and $R_4$ hydrogen, chlorine, methyl or methoxy, as substituent $R_5$ hydrogen, methyl or phenyl, as substituents $R_6$ to $R_8$ either three hydrogen atoms or two hydrogen atoms and one chlorine atom, one alkyl or alkoxy group with 1 to 5 carbon atoms, one cyano or phenyl group or an alkanoylamino or alkoxycarbonylamino group with 2 to 5 carbon atoms or one hydrogen and two chlorine atoms.

In general, the optionally substituted alkyl radicals $R_1$ and/or $R_2$ are to be understood as being the methyl, ethyl, n-propyl, iso-propyl, n-butyl, iso-butyl, n-amyl, isoamyl or n-hexyl radical or the 2-hydroxyethyl, 2-cyanethyl, chloromethyl, 2-chlorethyl, aminocarbonylmethyl or benzyl radical.

Especially preferred compounds are of formula

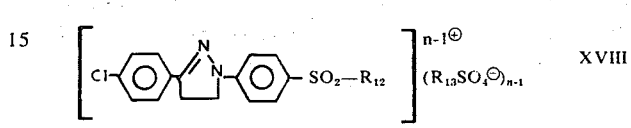

where $R_{12}$ signifies

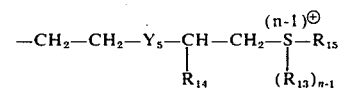

or

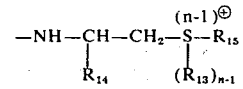

$R_{13}$ signifies methyl or ethyl, $R_{14}$ signifies hydrogen or methyl, $R_{15}$ signifies methyl or ethyl and $Y_5$ signifies —O—, —CO—O— or —CO—NH—.

The acylation of a compound of formula (II) in which $Y_2$ represents —O— with a carboxylic acid of formula (III) is carried out in accordance with conventional methods, for example as follows. The compound of formula (II) in which $Y_2$ represents —O— is dissolved or suspended in an inert organic solvent along with the carboxylic acid of formula (III), then an acid is added as catalyst, for example sulphuric, phosphoric, methanesulphonic, ethanesulphonic, benzenesulphonic or toluenesulphonic acid, or alternatively hydrogen chloride or hydrogen bromide gas or a salt of acid reaction such as zinc chloride, and esterification carried out to the end-point at, e.g., 0°C to 200°C, if necessary at increased or reduced pressure, and preferably under as far as possible anhydrous conditions, e.g. with the azeotropic removal of the water formed in the reaction. The ester thus formed can be isolated by one of the normal methods, for example by filtering with suction if it is present in suspension, by precipitation with a suitable precipitant and filtration with suction, by evaporation or distillation in water vapour of the solvent followed by filtration of the separated product with suction.

The acylation of a compound of formula (II) in which $Y_2$ represents an —N($R_9$)— group with a halide or anhydride of a carboxylic acid of formula (III) is carried out according to the conventional methods. It can be accomplished, for example, at temperatures from 0°C to 100°C in aqueous, aqueous-organic or organic medium (the organic solvent being selected from those which are inert to the reactants under the reaction conditions), or in the presence of an excess of the amine employed, provided it is liquid under the reaction conditions. The reaction can be carried out, for example, at 0°C to 60°C in aqueous-organic or organic medium in the presence of an acid-binding agent (an alkali-metal hydroxide, carbonate, bicarbonate or phosphate, calcium carbonate, magnesium oxide, pyridine, triethylamine or an excess of the amine).

A variant form of the present process consists in producing the halide of the carboxylic acid of formula (III) in the reaction medium itself and reacting it in the nascent state with a compound of formula (II) in which $Y_2$ signifies an —N($R_9$)—group. For this purpose an inorganic acid halide, for example an acid bromide or preferably an acid chloride, is used. Inorganic acid chlorides showing particularly good suitability are thionyl chloride, phosphorus trichloride and phosphorus oxychloride. In addition phosphorus pentachloride, phosphorus tribromide and phosphorus pentabromide are well suitable.

The reactants are suspended or dissolved in an inert organic solvent and the suspension or solution set at a temperature between about 0°C and 50°C with an inorganic acid chloride, in particular phosphorus trichloride, or with phosphorus pentachloride. It is of great advantage to employ such a large excess of amine or, additionally to the amount of amine necessary for the reaction, such a large amount of a tertiary base, e.g. pyridine, trimethylamine or dimethylaniline, that all the acid liberated in the reaction is bound, i.e. at least one equivalent of amine and one equivalent of the tertiary base or at least two equivalents of the amine relative to the acid equivalents of the compound of formula (III) for condensation. The condensation of the carboxylic acid with the amine is then carried through to completion at temperatures between about 0°C and 100°C.

Examples of especially suitable inert organic solvents are petroleum ether and other liquid aliphatic hydrocarbons, halogenated, in particular chlorinated aliphatic hydrocarbons such as methylene chloride, chloroform, carbon tetrachloride, dichlorethane, aromatic hydrocarbons, halogenated or nitrated aromatic hydrocarbons such as benzene, toluene, xylene, chlorobenzene and nitrobenzene, aliphatic, cyclic or aliphatic aromatic ethers such as diethyl ether, di-isopropyl ether, dioxane, methoxybenzene etc.

The acylation of a compound of formula (II) in which $Y_2$ represents —O— with a halide or anhydride or anhydride of a carboxylic acid of formula (III) is also carried out in accordance with known methods. It can be conveniently effected in the presence of an inert organic solvent and preferably in the presence of an acid-binding agent at temperatures of, e.g., 0°C to 150°C. Examples of suitable inert solvents are those suitable for the reaction of the halides or anhydrides of the carboxylic acids of formula (III) with the compounds of formula (II) in which $Y_2$ stands for an —N($R_9$) group. Examples of acid-binding agents are inorganic compounds such as the alcoholates, hydroxides, carbonates and bicarbonates of alkali-metals, the alcoholates, hydroxides, oxides and carbonates of alkaline-earth metals, and organic, preferably tertiary, amines such as trimethyl amine, which is employed as a solution or a gas, triethylamine, tri-n-butylamine, pyridine, a mixture of pyridine bases, dimethyl- and diethylaminobenzene. It is preferable to employ an inert organic solvent with the compound of formula (II) alone at room temperature to about 100°C, or to work in the presence of an alkali-metal hydroxide or alcoholate or a tertiary base such as pyridine at 0°C to 40°C.

The reaction of a compound of formula (V) or formula (XI), in which M represents an equivalent of an alkali-metal (e.g. Na, K, Li), an alkaline-earth metal (e.g. Mg, Ca, Sr, Ba) or another metal (Pb, Ag), with a compound of formula (VI) or (XII) respectively, in which $R_{10}$ represents, for example, a halogen atom (Cl, Br, J), a sulphate, methylsulphate, ethylsulphate, methanesulphonate, ethanesulphonate, benzenesulphonate, 4-methylbenzenesulphonate or acetate radical, can be conveniently carried out by conventional methods in an inert organic solvent from room temperature to about 150°C, preferably from 40°C to 120°C, with subsequent isolation of the product. For this reaction the aforenamed solvents, with the exception of halogenated alkanes, are suitable.

The reaction of compounds of formula (VII) with compounds of formula (VIII) is carried out in accordance with known methods, advantageously in an inert solvent.

The reaction of compounds of formula (VII) in which $Z_1$ represents —CH=CH$_2$ can be conveniently carried out in the presence of a catalyst, and the reaction of compounds of formula (VII) in which $Z_1$ represents —$A_1$—$R_{10}$ can be conveniently carried out in the presence of a base.

The reaction of a compound of formula (VII) with a compound of formula (VIII) in which $m$ is 2 and $Y_3$ represents oxygen can be conveniently carried out in an inert organic solvent, e.g. an ether or ketone, or in an optionally halogenated or nitrated hydrocarbon, at temperatures from room temperature to 150°C, preferably at 50°C to 100°C, in the presence of an alkali-metal hydroxide or alcoholate. An excess of the alcohol of formula (VIII) employed can be used as solvent and a small amount of water does not interfere with the progress of the reaction. The compounds of formula (I) thus formed, in which $q$ is O, can be isolated by one of the conventional methods, for instance by filtration with suction if present in suspension, by precipitation with a suitable precipitant and filtration with suction, by evaporation or distillation in water vapour of the solvent followed by filtration with suction of the separated product.

The reaction of a compound of formula (VII) in which $Z_1$ represents —CH=CH$_2$ with a thiole compound of formula (VIII) can be carried out, e.g., in a solvent which is inert to the reactants in the temperature region of 0°C to 200°C, preferably from room temperature to 150°C, without a catalyst, or preferably in the presence of a catalyst.

Examples of suitable inert solvents for this reaction are water, preferably in mixture with an organic solvent, and organic solvents such as ethers (diethyl ether, di-isopropyl ether, di-n-butyl ether, di-n-amyl ether, dioxan, 1,2-dimethoxyethane, 1,2-di-ethoxyethane, 1,2-di-n-butoxyethane, methoxy-benzene, ethoxybenzene), optionally halogenated aromatic hydrocarbons (benzene, toluene, xylene, ethyl benzene, chlorobenzene, ortho-dichlorobenzene, bromobenzene), amides (dimethyl formamide and acetamide, N-methyl pyrrolidone, phosphoric acid tri-(dimethylamide)), sulphoxides and sulphones (dimethyl sulphoxide, tetramethylene sulphone). Examples of suitable catalysts are copper acetate, mercury acetate, light, peroxides such as benzyl peroxide, cumene peroxide, acid substances, or preferably a substance of alkaline reaction such as ammonia, alkali-metal carbonates, hydroxides or alcoholates, primary, secondary or tertiary amines, quaternary ammonium hydroxide bases, e.g. methyl amine, dimethyl amine, trimethyl, triethyl, tri-n-butylamine, pyridine, piperidine, tetramethyl, tetraethyl and trimethyl benzyl ammonium hydroxide.

The esterification of a compound of formula (IX) in which $Z_2$ signifies —OH with an alcohol of formula (X) is carried out in conformance with conventional methods, for example by the following procedure. The carboxylic acid for esterification is entered into a mixture of an alcohol of formula (X) and an inert organic solvent, e.g. a hydrocarbon, a halogenated hydrocarbon, an ether or an excess of the alcohol itself, after which the catalyst is added, which may be an acid such as sulphuric, phosphoric, methanesulphonic, ethanesulphonic, benzenesulphonic or toluenesulphonic acid, hydrogen chloride or hydrogen bromide gas, or a salt of acid reaction such as zinc chloride. The esterification reaction is then carried through to the end-point at, e.g., 0° to 200°C, if necessary under increased or reduced pressure and preferably under as nearly as possible anhydrous conditions, e.g. with azeotropic removal of the water formed in the reaction. The resulting ester can be isolated by one of the methods referred to above.

The reaction of a compound of formula (IX) in which $Z_2$ signifies F, Cl or BR or of a compound of formula (XIII) with an alcohol of formula (X) or an amine of formula (XIV) can be carried out effectively in the presence of an inert solvent and preferably an acid-binding agent at temperatures of, e.g. 0° to 150°C, in accordance with conventional methods.

It is preferable to work with an excess of the alcohol, which then serves both as reactant and reaction medium, and at temperatures in the range of 60° to 150°C when no acid-binding agent is used or at 0° to 40°C in the presence of an alkali-metal hydroxide or alcoholate or a tertiary amine such as pyridine.

The acid halides of formulae (IX) and (XII) and the halides of the carboxylic acids of formula (III) can be produced by the known methods. For instance, the corresponding carboxylic acids can be taken as starting materials and treated at, e.g. room temperature to 150°C with phosgene, oxalyl chloride, thionyl chloride, phosphorus oxychloride, phosphorus oxybromide, phosphorus trichloride or phosphorus pentachloride, if necessary in the presence of an inert solvent and preferably in the presence of a base such as pyridine.

The methyl, ethyl or butyl esters of carboxylic acids of formulae (III) or (IX) can be transesterified with an alcohol of formulae (II) or (IX) in analogy with known methods in the presence of an alkali-metal compound of the same alcohol. Effectively, a substantial excess of the alcohol of formula (II) or (X) is employed in the presence of an alcoholate of the same alcohol at elevated temperature, e.g. from 120° to 160°C, with distillation of the liberated alkanol if necessary. It is advisable to add the catalyst in small portions, e.g. in three portions, and to work at a quantitative ratio of about 0.025 mols of alcoholate to 1 mol of the ester. The resulting compounds of formula (I) in which $q$ is O can be isolated by one of the methods referred to above.

The reaction of compounds of formula (XV) with compounds of formula (XVI) for the formation of pyrazoline compounds of formula (I) in which $q$ is 0 is carried out in accordance with conventional methods, for example in aqueous or aqueous-organic medium at pH values from 1 to 10, at temperatures from 0° to 150°C, preferably 60° to 120°C, and if necessary in the presence of an acid-binding agent; the exact pH value depends on the acid-sensitivity of the reactants and the peferred pH region may range from 2 to 5 to 3 to 7. Organic solvents miscible with water are suitable, e.g. acetic acid, alcohols such as methanol and ethanol, and ethers such as β-ethoxyethanol and β-ethoxyethyl acetate.

If Q in compounds of formula (XV) represents Hal, it is preferably chlorine; if Q represents the radical of an amine suitable for the formation of a Mannich base, it signifies in particular the radical of a lower primary or secondary aliphatic amine in which the lower alkyl radicals may have the aforenamed meanings; $R_{11}$ then represents preferably hydrogen.

The compounds of formula (XVII) are reacted with the compounds of formula (XVI) under the same conditions as the compounds of formula (XV).

The compounds of formula (XVII) can be produced in accordance or in analogy with known methods.

Examples of suitable alkylating agents are epoxy compounds such as ethylene oxide, propylene oxide, epichlorohydrin, the esters of strong mineral acids and organic sulphonic acids, alkyl chlorides alkyl bromides, alkyl iodides, aralkyl halies, the esters of lower alkanesulphonic acids, e.g. methane-, ethane- and butanesulphonic acid, the esters of benzenesulphonic acids which may be further substituted, e.g. the methyl, propyl and n-butyl esters of benzenesulphonic acid, 2- and 4-methylbenzenesulphonic acid, 4-chlorobenzenesulphonic acid, 3- and 4-nitrobenzenesulphonic acid, methyl chloride, methyl bromide, methyl iodide, ethyl chloride, benzyl chloride, chloracetic amide, diethyl sulphate, dimethyl sulphate, the methyl esters of lower alkanesulphonic acids and benzenesulphonic acids, acrylic amide and hydrogen chloride.

The treatment with alkylating agents of formula (IV) is carried out according to conventional methods at temperatures which may effectively range from 0° to 150°C, preferably from about 15° to 110°C, in an inert solvent, e.g. an ether, ketone, aromatic hydrocarbon, halogenated or nitrated aromatic hydrocarbon, a lower alkanecarboxylic acid, or in particular a lower alcohol such as methanol, in the presence or absence of water or in an excess of the alkylating agent.

The starting compounds of formulae (II) to (XVII) are known or can be produced by known methods, for example as described in "Organic Reactions", Vol. I, pp. 304–341, and Vol. 16; Olah, "Friedel-Crafts and Related Reactions", in particular Vol. III, part 1; Kirk and Othmer, "Encyclopedia of Chemical Technology", pp. 147–149; "The Chemistry Heterocyclic Compounds" Vol. 22 (1967), Interscience Publishers, pp. 177–278; and Houben-Weyl, "Methoden der organischen Chemie", 4. Auflage, Vol. IX, pp. 123–128 (1955), French Pat. No. 1,354,629 and W. German Pat. No. 1,104,483.

The hydrazine compounds of formula (XVI) can be produced in analogy with the known methods, formation of the radical of formula

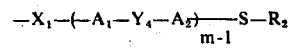

being accomplished in accordance with the aforedescribed methods.

The sulphonium compounds thus formed often separate out of the reaction medium and can be filtered with suction, washed and dried. If this is not the case, the solvent can be removed by distillation or the reaction mixture diluted with a suitable agent such as petroleum ether.

The compounds of formula (I) are isolated in accordance with standard methods, e.g. by filtration with suction, if necessary after dilution of the reaction medium, by precipitation or salting out with a liquid precipitant or other suitable agents, by evaporation of the solvent and filtration with suction, etc.

The new pyrazoline compounds of formula (I) have excellent properties as optical brightening agents and are especially suitable for the optical brightening of a wide variety of organic polymeric materials. By "organic polymeric materials" are understood natural fibres such as cotton and wool, but more especially synthetic fibre-forming polymers such as polyesters, polyamides, polyurethanes, polyolefins (polyethylene, polypropylene), polyvinyl acetate, polyvinyl chloride, polyvinylidene chloride, polyacrylonitrile, modified polyacrylonitrile, cellulose triacetate, secondary cellulose acetate, and polystyrene.

The compounds of formula (I) can be applied by any of the normal methods, for example in the form of solutions in organic solvents or as aqueous solutions or dispersions.

The compounds of formula (I) in which $q$ is 0 are especially suitable for the optical brightening of secondary cellulose acetate and cellulose triacetate and of synthetic polyamide fibres from aqueous dispersion, while the leading area of application for compounds of formula (I) in which $q$ is 1 or 2 is the optical brightening of acrylonitrile polymers, in particular polyacrylonitrile fibres, and of fibres containing acrylonitrile, from aqueous solution or in the spinning solution. By "acrylonitrile polymers" are understood in particular polymers composed of more than 80 % of acrylonitrile and copolymers composed of 80 to 95 % of acrylonitrile and 20 to 5 % of vinyl acetate, vinyl pyridine, vinyl chloride, vinylidene chloride, acrylic acid, acrylic acid ester, methacrylic acid, methacrylic acid ester, etc.

Depending on the method of application, the amount of the disclosed optical brightener employed may range from 0.001 to 0.5 %, preferably from 0.01 to 0.2 %, in relation to the weight of the material for brightening. These compounds can be applied alone or in combination with other optical brighteners and in the presence of surface-active agents such as detergents and carriers, and of finishing agents for antistatic and crease resistant finishes.

Brilliant, intense optical white effects with good light and wet fastness are obtained.

In the following Examples the parts and percentages are by weight and the temperatures in degrees centigrade. The parts by volume relate to the parts by weight as milliliters to grams. The melting points are uncorrected.

EXAMPLE 1

7.5 Parts of 1-(4'-β-chlorcarbonyl ethylene sulphonyl phenyl)-3-(4''-chlorophenyl)-Δ²-pyrazoline are stirred into 15 parts by volume of β-methyl thioethanol and the mixture raised to 60°. The acid chloride goes into solution and hydrogen chloride gas is evolved. The reaction mixture is cooled, diluted with 30 parts by volume of 95 % alcohol, and the precipitate filtered off with suction. After drying at 80° the ester of formula

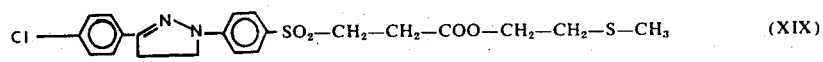

is obtained in a yield of 7.1 parts as an almost colourless substance with m.p. 119°–121°. On recrystallization from 2-ethoxyethanol and then from aqueous dimethyl formamide, the pure product with m.p. 124°–125° is obtained.

The starting compound used in this procedure can be produced as follows. 14 parts of 1-(4'-β-carboxyethylsulphonylphenyl)-3-(4''-chlorophenyl)-Δ²-pyrazoline are stirred with 15 parts by volume of oxalyl chloride at room temperature. After the addition of 0.1 part of dimethyl formamide an energetic reaction takes place. The reaction mixture turns thick and dry toluene (40 parts by volume) is added. The temperature is raised to 60°–70°, then the mixture is allowed to cool. The precipitated product is filtered, washed with petroleum ether (boiling range 40°–60°) and dried at 80°. 13.9 Parts of a pale yellow substance with m.p. 129°–131° are obtained.

EXAMPLE 2

A mixture of 3 parts of the pyrazoline ester of formula (XIX), 2 parts of dimethyl sulphate and 52 parts of dioxan is boiled for 1 hour with stirring and reflux. The sulphonium salt of formula

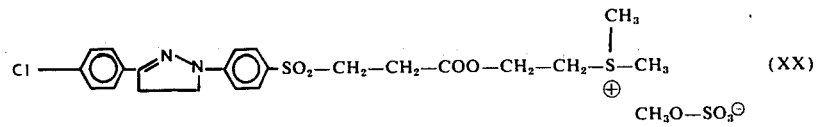

settles out as a pale yellow water-soluble oil in a yield of 4 parts.

EXAMPLE 3

5 Parts of 1-(4'-vinylsulphonylphenyl)-3-(4''-chlorophenyl)-Δ²-pyrazoline are mixed with 52 parts of dioxane, 12 parts by volume of ethanethiol and 0.7 parts of 33% sodium hydroxide solution. The mixture is raised to the boil and boiled for 30 minutes with reflux and constant stirring. After distillation of the solvent at reduced pressure, the crude sulphide of formula

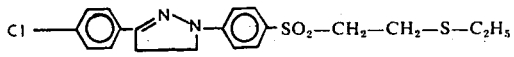 (XXI)

is obtained as a pale yellow solid substance in a yield of 5.5 parts. This is recrystallized from 2-ethoxyethanol to give the pure sulphide of formula (XXI), m.p. 140°–143°, in a yield of 4.1 parts.

EXAMPLE 4

A mixture of 1 part of the sulphide of formula (XXI) and 2 parts by volume of dimethyl sulphate is stirred for 30 minutes at 60°. After the addition of 15 parts of water the batch is stirred continuously overnight. The procedure results in 17 parts by volume of a 6 % solution of the sulphonium salt of formula

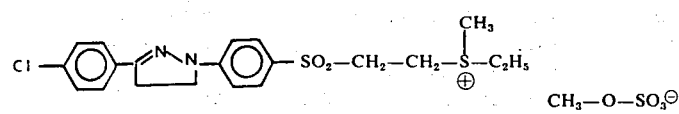 (XXII)

EXAMPLE 5

A mixture of 3 parts of 1-(4'-vinylsulphonylphenyl)-3-(4''-chlorophenyl)-$\Delta^2$-pyrazoline and 11.2 parts of 2-methyl thioethanol is raised to 70°–75°, on which 1.1 parts of a 2/normal sodium hydroxide solution are added, the temperature being maintained at 70°–75° until everything has gone into solution. The solution is allowed to cool to room temperature and 10 parts of water are added to cause precipitation of the pyrazoline derivative of formula

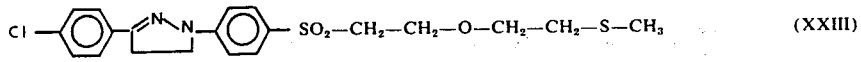 (XXIII)

This is obtained in good yield as a pale yellow solid of m.p. 113°–115°. By recrystallization from 2-ethoxyethanol the compound is obtained in the pure form in which it melts at 115°–117°.

EXAMPLE 6

If the methyl thioethanol used in Example 5 is replaced by the equivalent amount of thiodiglycol, the pyrazoline derivative of formula

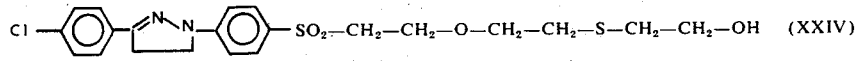 (XXIV)

is obtained in the form of a solid whitish substance with m.p. 125°–126°.

EXAMPLE 7

A mixture of 2 parts of the pyrazoline derivative of formula (XXIII), 1.33 parts of dimethyl sulphate and 21 parts of dioxan is held at the boil for 10 minutes with reflux. During the treatment the pyrazoline derivative of formula

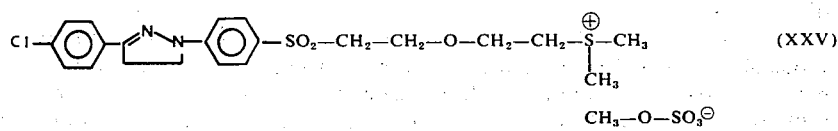 (XXV)

is precipitated in the form of a pale yellow water-soluble oil.

EXAMPLE 8

If the 2 parts of the pyrazoline derivative of formula (XXIII) in Example 7 are replaced by the equivalent amount of the pyrazoline derivative of formula (XXIV) and only 10 parts of dioxan are used as solvent, the pyrazoline derivative of formula

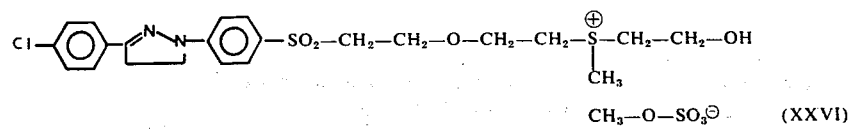 (XXVI)

is obtained in the form of a water-soluble oil.

EXAMPLE 9

A mixture of 3 parts of 1-(4'-carboxymethyl)-3-(4''-chlorophenyl)$\Delta^2$-pyrazoline, 4.3 parts of oxalyl chloride and 18 parts of toluene is heated to 40° and held at this temperature until the evolution of hydrogen chloride ceases. After cooling to room temperature the precipitate is isolated by filtration. It is stirred into 16 parts of dry acetone to give a suspension, to which 3 parts of 2-methyl thioethanol are added. The suspension is held at 40° for 10 minutes, allowed to cool to room temperature and diluted with water which leads to precipitation of the pyrazoline derivative of formula

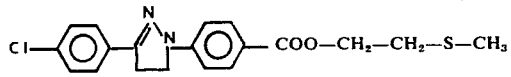

in the form of a solid substance, m.p. 143°–146°, and in good yield.

EXAMPLE 10

The pyrazoline derivative of formula (XXVII) is treated by the method described in Example 7. A solid, pale yellow substance of formula

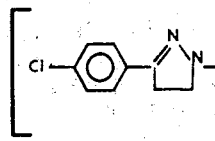

is obtained in good yield (m.p. 178°–181°, with decomposition). The pure compound obtained after recrystallization from acetone melts at 178°–180°.

EXAMPLE 11

A mixture of 8 parts of the sodium salt of 1-(4'-carboxyphenyl)-3-(4''-chlorophenyl)-$\Delta^2$-pyrazoline, 6.4 parts of chloracetic acid-β-methyl thioethylester, 3.8 parts of triethylamine and toluene is held under reflux for 4 hours and then allowed to cool to room temperature. The precipitated pyrazoline of formula

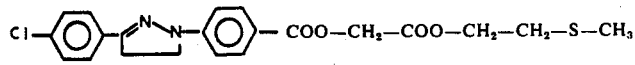

is filtered with suction and dried. The crude product thus formed melts at 123°–127°. On purification from 2-ethoxyethanol as pale yellow crystals it melts at 131°–132°.

EXAMPLE 12

A mixture of 2 parts of the pyrazoline of formula (XXIX) and 1.33 parts of dimethyl sulphate in 20 parts of dioxan is prepared, raised to the boil, boiled for 1 hour and then allowed to cool. It is set with a saturated sodium chloride solution and zinc chloride, on which an oily yellow precipitate separates from the medium. This is filtered with suction and dried (m.p. 167°–169°, with decomposition). Recrystallization from acetone gives the pure product of formula

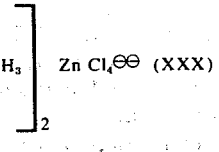

which melts at 169°–170° with decomposition.

EXAMPLE 13

A batch of 15.9 parts of 1-(4'-chlorosulphonyl-phenyl)-3-(4''-chlorophenyl)-$\Delta^2$-pyrazoline, 4.73 parts of β-ethyl thioethylamine, 3.56 parts of pyridine and 43 parts of dimethyl formamide is stirred for 1 hour at room temperature. The resulting solution is run into 150 parts of water and the precipitate is filtered with suction, washed with water and recrystallized from 2-ethoxyethanol. The sulphonic acid amide of formula

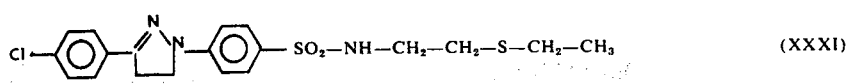

is obtained in a yield of 10 parts and in the form of a pale yellow solid with m.p. 139°–141°.

EXAMPLE 14

A reaction mixture consisting of 4 parts of the sulphonic acid amide of formula (XXXI), 1.35 parts of dimethyl sulphate and 31 parts of dioxan is held at the boil with reflux for 1 hour. As the batch cools the sulphonium salt of formula

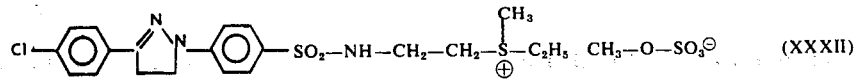

settles out in pale yellow crystalline form. It is isolated by filtration with suction, washed with acetone and dried at 80°. The salt, m.p. 218°–220°, is obtained in a yield of 3.1 parts.

EXAMPLE 15

5.32 Parts of 1-(4'-carboxyphenyl)-3-(phenyl)-Δ² -pyrazoline are added to 25 parts of toluene and 1.8 parts of oxalyl chloride. The mixture is stirred at 40° until no further hydrogen chloride is developed. It is then cooled and filtered. The acid chloride formed is stirred into 30 parts of dry acetone containing 5 parts of methyl thioethanol, the mixture held at the refluxing temperature for 10 minutes and then allowed to cool to room temperature. The pyrazoline compound of formula

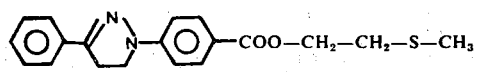

thus formed is filtered and washed with a little acetone. 4.3 Parts of pale yellow needles, m.p. 114°–115°, are obtained.

EXAMPLE 16

A mixture of 3 parts of the pyrazoline compound of formula (XXXIII), 1.73 parts of dimethyl sulphate and 15 parts of dioxan is boiled for 1 hour. On cooling the sulphonium compound of formula

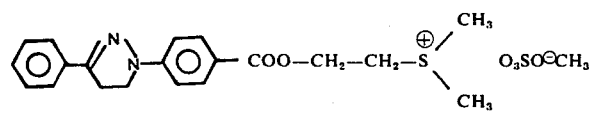

settles out as a yellow product, m.p. 186°–187°. After recrystallization from aqueous dioxan the pure product, m.p. 194°–195°, is obtained.

EXAMPLE 17

A mixture of 5 parts of 1-p-vinylsulphonylphenyl-3-(3',4'-dichlorophenyl)-Δ²-pyrazoline and 12.5 parts of methyl thioethanol is raised to 70°–75°, set with 0.5 parts by volume of a 33 % sodium hydroxide solution and held further at 70°–75° until dissolving is complete. It is then cooled to room temperature. On dilution with 12 parts of water the pyrazoline compound of formula

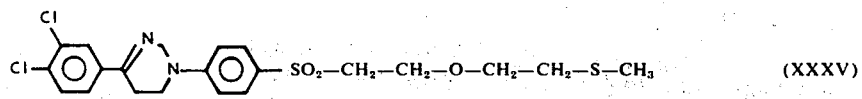

is precipitated in the form of a solid pale yellow product (5.2 parts, m.p. 98°–104°). On recrystallization from "Cellosolve" the pure product of m.p. 101°–102° is obtained.

EXAMPLE 18

(XXXIII)

A mixture of 1 part of the compound of formula (XXXV), 0.4 parts of limethyl sulphate and 10 parts of dioxan is held at the refluxing temperature for 1 hour; during this time the pyrazoline compound of formula

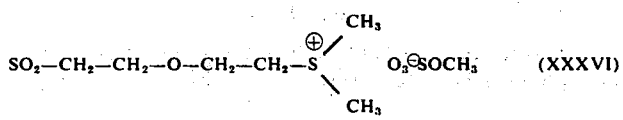

settles out as a pale yellow water-soluble oil.

EXAMPLE 19

If the 11.2 parts pf 2-methyl thioethanol in Example 5 are replaced by the equivalent amount of 1-methyl-2-

(XXXIV)

ethyl thioethanol, the pyrazoline compound of formula

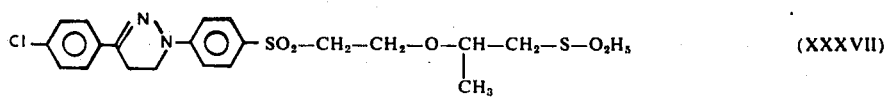

is obtained with m.p. 102°–103°.

EXAMPLE 20

A mixture of 2 parts of the compound of formula (XXXVII), 2.6 parts of dimethyl sulphate and 20 parts of dioxan is boiled for 1 hour with reflux. During this time the compound of formula

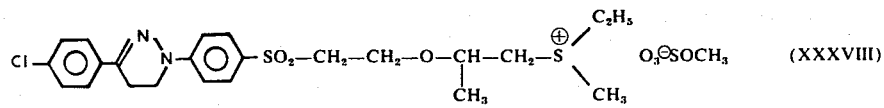

settles out in the form of a pale yellow water-soluble oil.

EXAMPLE 21

A suspension of 4.7 parts of 1-(4'-β-chlorocarbonylethylsulphonylphenyl)-3-(4''-chlorophenyl-Δ²-pyrazoline in 20 parts by volume of dioxan is set with 2.2 parts of β-ethyl thioethylamine. The mixture is raised to 60° and held at this temperature for 30 minutes. After cooling to 25° 5 parts of water are added, causing precipitation of the pyrazoline compound of formula

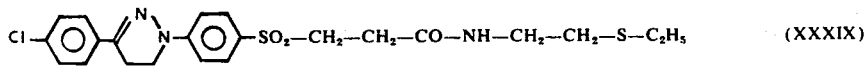

After filtration and drying at 70° a solid pale yellow substance with melting point 164°–167° is obtained in a yield of 5.5 parts. Recrystallization from 2-ethoxyethanol gives the pure product which melts at 166°–167°.

EXAMPLE 22

A mixture of 2 parts of the compound of formula (XXXIX), 0.5 parts by volume of dimethyl sulphate and 15 parts by volume of dioxan is boiled for 1 hour with stirring and reflux. The mixture is then cooled and the dioxan decanted from the compound of formula

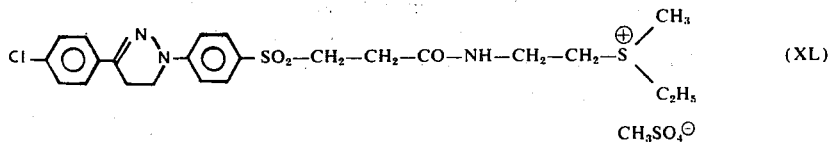

which is present as a pale yellow oil.

EXAMPLE 23

The pyrazoline compound of formula

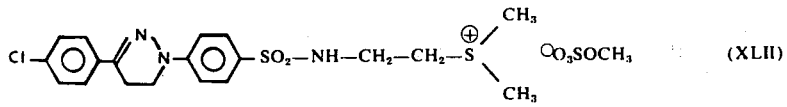

with m.p. 163°–164° is produced in an analogous manner to the pyrazoline compound of formula (XXXI).

EXAMPLE 24

The pyrazoline compound of formula

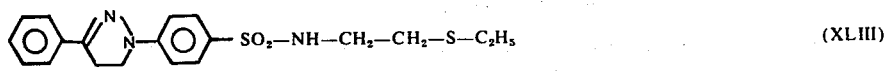

with m.p. 184°–190° is produced in an analogous manner to the pyrazoline compound of formula (XXXII) (Example 14).

EXAMPLE 25

10 Parts of 1-(4'-chlorosulphonylphenyl)-3-phenyl-Δ²-pyrazoline, 10 parts of β-ethylthioethylamine (from ethylene imine and ethanethiole, and 20 parts of dimethyl formamide are mixed for 1 hour at room temperature. The resulting solution is diluted with 100 parts of water. The precipitate formed is filtered, washed with water and crystallized from 2-ethoxyethanol. 8.2 Parts of the compound of formula are obtained as a pale yellow solid substance with m.p. 135°–137°.

A solution of 3 parts of the compound of formula (XLIII) described in Example 25 and 1.46 parts of dimethyl sulphate in 20 parts of dioxan is boiled for 1 hour with reflux. The sulphonium salt of formula

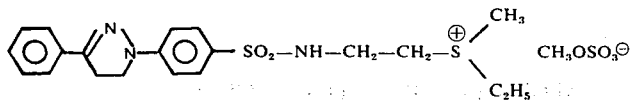

(XLIV)

settles out in the form of a pale yellow water-soluble oil.

The following Table specifies further compounds according to this invention which agree with the formula

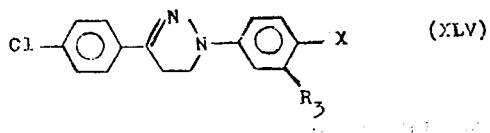

(XLV)

with cold demineralized water, and dried at 80°. The fabric thus treated shows a brilliant white effect in comparison with an unbrightened polyacrylonitrile fabric.

APPLICATION EXAMPLE B

100 Parts of a fabric of secondary cellulose acetate are treated with 4000 parts of a solution containing 0.5 parts of the product produced as in Example 1 (in the form of a solution in 2-ethoxyethanol) and 20 parts of a fatty alkyl polyglycol acetate. The fabric is entered at 40°, the solution raised to 80° in 30 minutes and held at this temperature for a further 30 minutes. On removal the fabric is rinsed thoroughly with demineralized water and dried at 80°. The treatment imparts a brilliant white effect to the cellulose acetate fabric.

APPLICATION EXAMPLE C

Table

| Example No. | $R_3$ | X | Melting point (appearance) | Fluorescence shade of the optical brightening effect on | |
|---|---|---|---|---|---|
| | | | | polyacrylonitrile fiber | secondary cellulose acetate |
| 27 | H | $-SO_2-CH_2-CH_2-COO-\underset{\underset{CH_3}{\mid}}{CH}-CH_2-S-CH_2-\bigcirc$ | (oil) | — | — |
| 28 | H | $-SO_2-CH_2-CH_2-COO-\underset{\underset{CH_3}{\mid}}{CH}-CH_2-\underset{\underset{CH_3}{\mid}}{\overset{\oplus}{S}}-CH_2-\bigcirc\ CH_3SO_4^\ominus$ | (oil) | neutral | — |
| 29 | H | $-SO_2-CH_2-CH_2-COO-\underset{\underset{CH_3}{\mid}}{CH}-CH_2-S-C_2H_5$ | 145–147° | — | reddish |
| 30 | H | $-SO_2-CH_2-CH_2-COO-\underset{\underset{CH_3}{\mid}}{CH}-CH_2-\underset{\underset{CH_3}{\mid}}{\overset{\oplus}{S}}-C_2H_5\ CH_3SO_4^\ominus$ | (oil) | reddish | — |
| 31 | Cl | $-SO_2-NH-CH_2-CH_2-S-C_2H_5$ | 139–141° | — | — |
| 32 | Cl | $-SO_2-NH-CH_2-CH_2-\underset{\underset{CH_3}{\mid}}{\overset{\oplus}{S}}-C_2H_5\ CH_3SO_4^\ominus$ | 213–217° | — | — |
| 33 | H | $-SO_2-CH_2-CH_2-COO-CH_2-CH_2-S-\underset{\underset{CH_3}{\mid}}{CH}-CH_3$ | 122–123° | — | reddish |
| 34 | H | $-SO_2-CH_2-CH_2-COO-CH_2-CH_2-\underset{\underset{CH_3}{\mid}}{\overset{\oplus}{S}}-\underset{\underset{CH_3}{\mid}}{CH}-CH_3\ \tfrac{1}{2}ZnCl_4^\ominus$ | (oil) | reddish | — |

APPLICATION EXAMPLE A

100 Parts of a polyacrylonitrile fabric are entered at 40° into a solution of 4000 parts containing 30 parts of a 10 % acetic acid solution and 0.5 parts of the product obtained as in Example 2 in the form of a 2 % solution. The temperature is increased to 90° in 30 minutes and maintained at 90°–95° for 1 hour. The fabric is then removed from the bath, rinsed well with hot and then 100 Parts of a polyacrylonitrile fabric are entered at 40° into an aqueous solution of 4000 parts set with 0.5 parts of the product disclosed in Example 4 in the form of a 5 % aqueous solution and 3 parts of acetic acid. The bath temperature is increased to 90° in 30 minutes and the temperature held at 90°–95° for a further hour. The fabric is then removed, rinsed with hot and then with cold demineralized water, and then dried at 80°. The treated fabric is appreciably whiter than an untreated fabric of the same fibre.

APPLICATION EXAMPLE D

100 Parts of a fabric of "Orlon" 75 polyacrylonitrile fibre are entered at 40° into a solution of 0.5 parts of the pyrazoline of formula (XXV) and 30 parts of 10 % acetic acid in 4000 parts of water. The pyrazoline is added in the form of an 8 % solution in aqueous dioxan. The bath is raised to 90°–95° in 30 minutes and held at this temperature for 1 hour. On removal the fabric is rinsed with demineralized water and dried at 80°. A brilliant optical brightening effect is obtained. With the pyrazoline of formula (XXVI) effects of comparable brilliance are obtained on polyacrylonitrile.

APPLICATION EXAMPLE E

100 Parts of a fabric of "Orlon " 75 polyacrylonitrile fibre are entered at 40° into a solution of 0.1 part of the pyrazoline of formula (XXVIII) and 30 parts of 10 % acetic acid in 4000 parts of water. The conditions of treatment are as given in Application Example D. A brilliant white is obtained on the substrate.

APPLICATION EXAMPLE F

100 Parts of a white fabric of "Banlon" (nylon 6.6 yarn) are entered at 40° into 5000 parts of an aqueous solution containing 20 parts of a powder detergent based on sodium dodecyl benzene sulphonate and 0.08 parts of the pyrazoline of formula (XXIX). The brightener compound is added as a fine dispersion prepared by running a 0.8 % solution in 2-ethoxyethanol into water. After the fabric has been entered the bath is brought to 60 in 15 minutes and held at this temperature for a further 15 minutes. The fabric is then removed, rinsed thoroughly in cold demineralized water and dried at 60°. In comparison with the untreated substrate the treated nylon fabric exhibits a brilliant white effect.

APPLICATION EXAMPLE C 100 parts of a white fabric of "Banlon" (nylon 6.6) yarn are entered at 40° into a aqueous solution of 4000 parts set with 0.2 parts of the pyrazoline of formula (XXIII), 30 parts of a 10 % aqueous acetic acid solution and 5 parts of a carboxymethylated oleyl decaglycol ether. The brightener is added as a fine dispersion formed by pouring a 0.1 % solution in 2-ethoxyethanol into an excess of water. The bath is raised from 40° to 90°–95° in about 30 minutes and the fabric treated further for 30 minutes at this temperature, with subsequent thorough rinsing in demineralized water and drying. A brilliant white effect is obtained.

APPLICATION EXAMPLE H

100 Parts of a fabric of "Dicel" secondary cellulose acetate fibre are entered at 40 into an aqueous solution of 4000 parts containing 5 parts of a carboxymethylated oleyl decaglycol ether and 0.5 parts of the pyrazoline of formula (XXIII), which is added as a 0.1 % solution in 2-ethoxyethanol. The temperature is raised to 80° in about 30 minutes and treatment continued at this temperature for 30 minutes. On removal the fabric is rinsed in hot and then in cold demineralized water and dried at 80°. A good whitening effect is obtained compared with untreated fabric.

APPLICATION EXAMPLE I

100 Parts of a fabric of "Tricel" cellulose triacetate fibre which has been scoured and then bleached with an acid sodium chlorite (NaClO$_2$) solution are conveyed into 4000 parts of an aqueous solution containing 5 parts of a carboxymethylated oleyl decaglycol ether and 0.5 parts of the pyrazoline of formula (XXIV), added in the form of a 0.1 % solution in 2-ethoxyethanol. The bath is raised to 90°–95° in 30 minutes and held at this temperature for 30 minutes. After removal the fabric is rinsed well with demineralized water and dried at 80°. It displays a good optical brightening effect.

APPLICATION EXAMPLE J

100 Parts of a fabric of "Orlon" 75 polyacrylonitrile fibre are entered at 40° into a solution of 2 parts of the pyrazoline of formula (XXXII) and 30 parts of 10% acetic acid in 4000 parts of water, the pyrazoline being added as an 8 % solution in aqueous dioxan. The bath is raised to 90°–95° in 30 minutes and held at this temperature for 1 hour, after which the fabric is removed, rinsed with demineralized water and dried at 80°. A brilliant optical white is obtained.

APPLICATION EXAMPLE K

100 Parts of a fabric of "Dicel" secondary cellulose acetate fibre are entered at 40° into an aqueous solution of 4000 parts containing 0.5 parts of the pyrazoline of formula (XXXI), added as a 0.1 % solution in 2-ethoxyethanol, and 5 parts of a carboxymethylated oleyl decaglycol ether. The bath is brought to 80° in about 30 minutes, the fabric treated for 30 minutes at this temperature and then removed. It is thoroughly rinsed in hot and then in cold demineralized water and dried at 80°. A good degree of whiteness is shown by the fabric compared with the untreated substrate.

APPLICATION EXAMPLE L

5 Parts of a white fabric of "Orlon" 75 polyacrylonitrile fibre are entered at 40° into 100 parts by volume of an aqueous solution containing 0.015 parts of the compound of formula (XXXVIII) and 0.15 parts of acetic acid. The bath is raised to 90° in 30 minutes and the fabric treated at 90°–95° for a further hour, with constant agitation. On removal the fabric is rinsed in hot and then in cold demineralized water and dried in an oven at 80°. The optically brightened Orlon 75 fabric has a distinctly whiter, more brilliant appearance than comparable unbrightened fabric.

APPLICATION EXAMPLE M

5 Parts of a white fabric of "Orlon" 75 polyacrylonitrile fibre are entered at 40° into 200 parts by volume of an aqueous solution containing 0.005 parts of the pyrazoline compound of formula (XXXVI) and 0.15 parts of acetic acid. The fabric is mechanically agitated while the bath is raised to 90° in 30 minutes and during a further hour at 90°–95°. It is then removed from the bath, rinsed in hot and then in cold demineralized water and oven dried at 80°. A brilliant white effect is obtained.

APPLICATION EXAMPLE N

5 Parts of a white fabric of "Dicel" secondary cellulose acetate fibre are entered at 40° into 200 parts by volume of an aqueous solution containing 5 parts of the compound of formula (XXXV) and 1 part of the chloracetate of an alkylene oxide condensation product, the brightener compound being added as a 0.1 % solution in 2-ethoxyethanol. The bath is brought to 80° in 15 minutes and held at this temperature for a further 30 minutes, the fabric being mechanically agitated throughout the treatment. On removal it is rinsed well with demineralized water and air dried at 80°. A brilliant white effect is obtained.

APPLICATION EXAMPLE O

5 Parts of a white fabric of "Orlon" 75 polyacrylonitrile fibre are entered at 40° into 200 parts by volume of an aqueous solution set with 0.01 part of the pyrazoline compound of formula (XXXIII) and 0.15 parts of acetic acid. The temperature is increased to 90° in 30 minutes and the bath held at 90°–95° for a further hour, with constant agitation of the fabric. The treatment is followed by rinsing with hot and then with cold demineralized water and air drying at 80°. The treated fabric exhibits greater brilliancy and whiteness than a comparable untreated fabric.

APPLICATION EXAMPLE P

5 Parts of a white fabric of "Orlon" 75 polyacrylonitrile fibre are entered at 40° into 200 parts by volume of an aqueous solution containing 0.025 parts of the compound of formula (XLIV) and 0.15 parts of acetic acid. The bath is raised to 90° in 30 minutes and held for a further hour at 90°–95°, the fabric being mechanically agitated throughout. Thorough rinsing with hot and then cold demineralized water and oven drying at 80° complete the treatment. A pronounced white effect is obtained on the fabric.

What is claimed is:

1. A compound of the formula

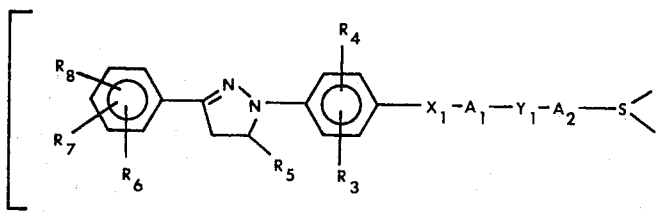

where $X_1$ is $-SO_2-$, $-CO-O$ or $-SO_2-NH-$,
$Y_1$ is $-O-$, $-CO-O$ or

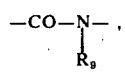

$A_1$ and $A_2$ are each $-CH_2-CH_2-$ or $$-\underset{\underset{CH_3}{|}}{CH}-CH_2-,$$

$R_1$ is alkyl of 1 to 5 carbon atoms which may be monosubstituted by chlorine, hydroxyl, cyano, or aminocarbonyl; or phenyl,
$R_2$ is one of the groups specified for $R_1$ or together with $R_9$ forms an ethylene group,
$R_3$ and $R_4$ each is hydrogen, chlorine, methyl or methoxy,
$R_5$ is hydrogen, methyl or phenyl,
either two of $R_6$, $R_7$ and $R_8$ are hydrogen and the other is hydrogen, chlorine, alkyl or alkoxy of 1 to 5 carbon atoms, cyano, phenyl, or alkanoylamino or alkoxycarbonylamino of 2 to 5 carbon atoms, or one of $R_6$, $R_7$ and $R_8$ is hydrogen and the others are chlorine,
$R_9$ is hydrogen or unsubstituted alkyl of 1 to 5 carbon atoms,
$n$ is the integer 1 or 2,
$q$ is the number of radicals $R_1$ present, and Anion⁻ signifies an equivalent of a colorless anion.

2. The compound according to claim 1 of the formula

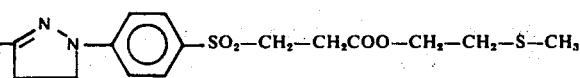

3. A compound according to claim 1 of the formula

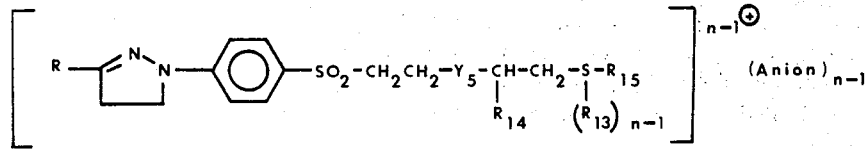

in which R is phenyl which is unsubstituted or disubstituted by chlorine or monosubstituted by chlorine, cyano, alkyl of 1 to 5 carbon atoms, alkoxy of 1 to 5 carbon atoms, phenyl, alkanoylamine of 2 to 5 carbon atoms or alkoxycarbonylamino,
$R_{13}$ is methyl or ethyl,
$R_{14}$ is hydrogen or methyl,
$R_{15}$ is methyl, ethyl or 2-hydroxyethyl,
$Y_5$ is $-O-$, $-COO-$ or $-CONH-$,
$n$ is 1 or 2, and
Anion signifies an equivalent of a colorless anion.

4. A compound according to claim 3 wherein R is phenyl which may be disubstituted by chlorine or monosubstituted by chlorine, cyano, alkyl or alkoxy.

5. A compound according to claim 4 wherein R is phenyl, p-chlorophenyl or 3,4-dichlorophenyl.

6. A compound according to claim 5 of the formula

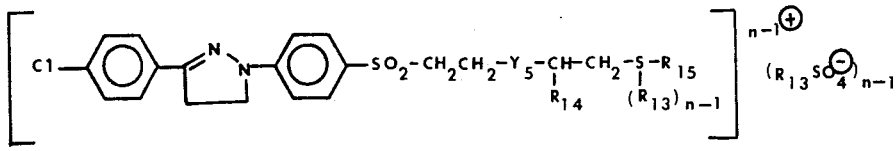

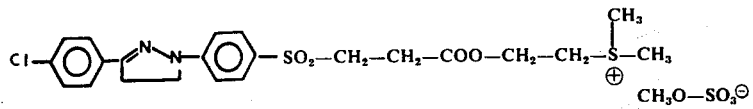

7. A compound of claim 5 in which R signifies p-chlorophenyl and Anion signifies the methylsulphate, ethylsulphate or chlorozincate anion.

8. A compound of claim 7 in which Anion signifies the methylsulphate or ethylsulphate anion.

9. A compound of claim 6 in which $R_{14}$ signifies hydrogen.

10. A compound of claim 6 of formula

11. A compound of claim 6 of formula

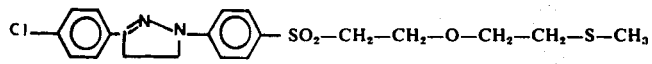

12. A compound of claim 6 of formula

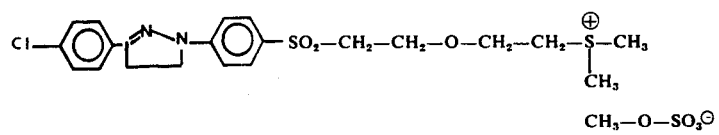

13. A compound of claim 6 of formula

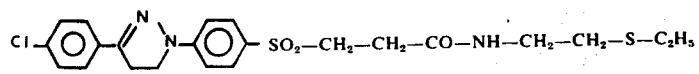

14. A compound of claim 6 of formula

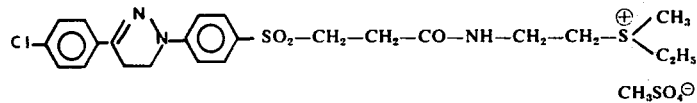

15. A compound of claim 6 of formula

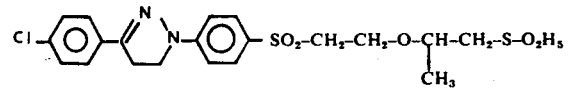

16. A compound of claim 1 of formula

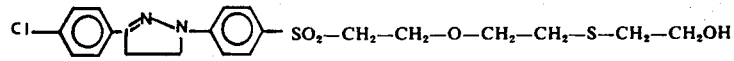

17. A compound of claim 6 of formula

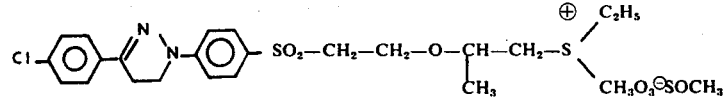

* * * * *